United States Patent
Wen et al.

(10) Patent No.: US 9,192,930 B2
(45) Date of Patent: Nov. 24, 2015

(54) PROCESS FOR REGENERATING A DEACTIVATED HETEROPOLYMOLYBDOPHOSPHORIC ACID CATALYST

(75) Inventors: Xin Wen, Shanghai (CN); Linghua Zuo, Shanghai (CN); Ge Luo, Shanghai (CN); Xiaoqi Zhao, Shanghai (CN); Yan Zhuang, Shanghai (CN); Xiaodong Chu, Shanghai (CN); Jingming Shao, Shanghai (CN)

(73) Assignee: SHANGHAI HUAYI ACRYLIC ACID CO. LTD., Shanghai (CN)

( * ) Notice: Subject to any disclaimer, the term of this patent is extended or adjusted under 35 U.S.C. 154(b) by 122 days.

(21) Appl. No.: 13/240,464

(22) Filed: Sep. 22, 2011

(65) Prior Publication Data

US 2012/0135856 A1 May 31, 2012

(30) Foreign Application Priority Data

Sep. 28, 2010 (CN) .......................... 2010 1 0295115

(51) Int. Cl.

| | |
|---|---|
| *B01J 38/00* | (2006.01) |
| *B01J 38/66* | (2006.01) |
| *B01J 23/00* | (2006.01) |
| *B01J 27/19* | (2006.01) |
| *B01J 27/199* | (2006.01) |
| *B01J 27/28* | (2006.01) |
| *B01J 37/00* | (2006.01) |
| *B01J 38/02* | (2006.01) |
| *B01J 38/12* | (2006.01) |
| *C07C 51/25* | (2006.01) |

(52) U.S. Cl.
CPC ............... *B01J 38/66* (2013.01); *B01J 23/002* (2013.01); *B01J 27/19* (2013.01); *B01J 27/199* (2013.01); *B01J 27/285* (2013.01); *B01J 37/0009* (2013.01); *B01J 37/0036* (2013.01); *B01J 38/02* (2013.01); *B01J 38/12* (2013.01); *C07C 51/252* (2013.01); *B01J 2523/00* (2013.01)

(58) Field of Classification Search
CPC ........ B01J 23/002; B01J 27/19; B01J 27/285; B01J 27/199; B01J 38/66; B01J 38/12; B01J 38/02; B01J 37/0036; B01J 37/0009; B01J 2523/00; B01J 2523/13; B01J 2523/15; B01J 2523/17; B01J 2523/51; B01J 2523/53; B01J 2523/55; B01J 2523/68; C07C 51/252; C07C 57/04
USPC ...................................................... 502/21–56
See application file for complete search history.

(56) References Cited

U.S. PATENT DOCUMENTS

| | | | |
|---|---|---|---|
| 4,111,832 A * | 9/1978 | Rohbock et al. ................. 502/24 |
| 4,814,305 A | 3/1989 | Kamogawa et al. | |
| 2001/0039240 A1 * | 11/2001 | Fukumoto et al. .............. 502/26 |
| 2009/0259070 A1 | 10/2009 | Ohishi et al. | |
| 2011/0160491 A1 * | 6/2011 | Dubois et al. ................. 568/486 |

FOREIGN PATENT DOCUMENTS

| | | |
|---|---|---|
| EP | 1142638 | 10/2001 |
| EP | 1192992 | 4/2002 |

OTHER PUBLICATIONS

European Search Report dated Nov. 10, 2011, issued in related European Patent Application No. EP 11183099.

* cited by examiner

*Primary Examiner* — Jennifer A Smith

(74) *Attorney, Agent, or Firm* — Kilpatrick Townsend & Stockton LLP

(57) ABSTRACT

The present invention provides a process for regenerating a deactivated heteropolymolybdophosphoric acid catalyst, comprising the steps of grinding the deactivated catalyst into particles having a particle size of 40 mesh or less, mixing the particles with a mixture comprising aqua ammonia, an aqueous solution containing ammonium ions and organic auxiliaries, kneading the same in a kneader to obtain a paste, drying the paste, molding the paste into cylindrical particles with a through hole in its longitudinal axis, and heating the paste in atmosphere at 350~450° C. for 1~10 hours to produce the generated catalyst.

9 Claims, No Drawings

PROCESS FOR REGENERATING A DEACTIVATED HETEROPOLYMOLYBDOPHOSPHORIC ACID CATALYST

CROSS-REFERENCES TO RELATED APPLICATIONS

This application claims the benefit of a priority application filed in China numbered 201010295115.x and filed on Sep. 28, 2010.

TECHNICAL FIELD

The present invention relates to a method for regenerating a deactivated heteropolymolybdophosphoric acid catalyst, and to the use of the regenerated catalyst in the selective oxidation of lower unsaturated aldehydes to prepare unsaturated acids.

BACKGROUND OF THE INVENTION

Producing methacrylic acid (MAA) by the use of isobutylene or t-butyl alcohol as a raw material via intermediate methacrolein (MAL) is one of the advanced routes for MAA preparation. There are a number of patents concerning the catalysts for producing MAA by MAL oxidation. All of the catalysts disclosed are heteropolymolybdophosphoric acid compounds (CN 100490973C, U.S. Pat. No. 4,256,914, U.S. Pat. No. 4,347,163, etc.). However, low degradation is the deficiency of these catalysts. Being subjected to an increased for an extended time, the catalyst may break down, with $MoO_3$ being generated, resulting in deteriorated activity.

Various approaches on the regeneration of the catalyst for recovering the catalytic activity have been studied in order to extend the lifespan of the catalyst. For example, U.S. Pat. No. 4,471,062 provided a method for the regeneration of the catalyst without discharging same, comprising the steps of sweeping the catalyst with an inert gas first, and then directly feeding an oxynitride at a of from about 100° C. to 400° C.

Chinese patent CN1451478A provided an online activation method comprising a step of feeding a gas mixture of oxygen, steam and nitrogen at a of from 290 to 400° C. once every half year or once a year.

Japanese Patent Publication JP 58-156351 disclosed a process to recover the catalytic activity by heat treatment, which process comprises a step of feeding an air flow containing at least 10% of steam by volume to the deactivated catalyst at a temperature of from 70 to 240° C.; however, such a process is ineffective with a catalyst with a destroyed structure.

U.S. Pat. No. 4,814,305 provides a method for regenerating a deactivated catalyst comprising the steps of dispersing the deactivated catalyst in water, adding a certain amount of aqueous ammonia at 50° C. and stirring for 1 hour, adding pyridine after drying and stirring the mixture obtained at 90° C. for 30 minutes, drying, and then calcining to produce a regenerated catalyst.

Japanese patent JP-A-2001-286763 provides a method for the regeneration of a deteriorated catalyst, comprising the steps of dispersing the deteriorated catalyst into water, adding a nitrogen-containing heterocyclic compound, ammonium nitrate and nitric acid at 70° C. to obtain a mixture, drying the mixture and then calcining the dried mixture.

Chinese patent CN101554593A discloses a method for the regeneration of a deactivated catalyst, comprising the steps of heat treating the deactivated catalyst at 350° C., mixing same with water, nitrate ions and ammonium ions, heat treating at 100° C., drying the mixture, and then calcining the dried mixture twice to obtain a regenerated catalyst.

Chinese patent CN100490975 discloses a method for the regeneration of a deactivated catalyst, comprising the steps of mixing the deactivated catalyst with water, nitrate ions and ammonium ions, aging same at 70° C. for 5 hours, and drying, molding and calcining the dried mixture to obtain a regenerated catalyst.

However, all these conventional methods for regeneration are cumbersome, time-consuming, and incapable of obtaining a regenerated catalyst having satisfactory catalytic activity.

BRIEF SUMMARY OF THE INVENTION

The object of the present invention is to provide a simple and easy process for regenerating a deactivated heteropolymolybdophosphoric acid catalyst.

In one aspect, there is provided a process for regenerating a deactivated heteropolymolybdophosphoric acid catalyst, comprising the steps of:

grinding the deactivated catalyst into particles having a particle size of 40 mesh or less; mixing said particles with a mixture consisting of aqua ammonia, an aqueous solution containing ammonium ion and organic auxiliaries, and kneading same in a kneader to obtain a paste; drying the paste and molding same into a cylindrical particle with a through hole in its longitudinal axis; and calcining in atmosphere at a of from 350 to 450° C. for 1~10 hours to produce a regenerated catalyst.

BRIEF DESCRIPTION OF THE DRAWINGS

Detailed Description of the Invention

The present invention concerns a simple and easy process for regenerating a deactivated heteropolymolybdophosphoric acid catalyst, which catalyst has a deteriorated catalytic activity because of its structure partially breaking down after being subjected to an increased for an extended operation time. According to the present invention, the catalyst to be regenerated is a deactivated catalyst whose structure has already deteriorated.

The deactivated catalyst is ground to a particle size of 40 mesh or less, and kneaded for 5~60 minutes with a mixture of aqua ammonia, aqueous solution containing ammonium ion and organic auxiliaries in a kneader to obtain a paste. The paste is dried for 1~24 hours and then molded into cylindrical particle with a through hole in its longitudinal axis, which is further calcined in atmosphere at 350~450° C. for 1~10 hours to produce a regenerated catalyst whose keggin structure of heteropoly acid is fully recovered.

According to the process described above, the aqueous solution containing ammonium ion can include in the aqueous solution members selected from the group consisting of ammonium nitrate, ammonium acetate, ammonium chloride, and ammonium carbonate, or the combination thereof. The molar ratio between ammonium ion in the mixture of aqua ammonia, aqueous solution containing ammonium ion and organic auxiliaries and the deactivated catalyst is in the range of 5:1~0.5:1. The of the mixture of aqua ammonia, aqueous solution containing ammonium ion and organic auxiliaries is controlled in the range of between 0 and 70° C., and the organic auxiliaries can be one or more selected from the group consisting of polyvinyl alcohol, pyridine, t-butyl alcohol, and polyethylene glycol.

The obtained regenerated catalyst is a cylindrical particle with a through hole in its longitudinal axis. In one embodiment, said cylindrical particle has an external diameter of from 4 to 8 mm, preferably from 4 to 6 mm, and more preferably 5 mm; an internal diameter (a diameter of through hole inside the cylinder) of from 0.5 to 3 mm, preferably from 1 to 2.5 mm, and more preferably 2 mm; and a length of from 3 to 8 mm, preferably from 4 to 6 mm, and more preferably 5 mm.

The catalyst of cylindrical particle with a through hole in its longitudinal axis generated according to the aforementioned process has a well-recovered catalytic activity, and is capable of being used in the selective gas phase oxidation reaction of MAL (methacrolein) to produce MAA (methacrylic acid). Said selective reaction is conducted by passing a preheated gas mixture through a stainless-steel stationary bed reactor having a diameter of 25 mm and a length of 3 m to perform the selective oxidization to produce MAA. Said gas mixture comprises MAL (a raw material), steam and air or a molecular oxygen-containing diluted gas mixture. With respect to the molecular oxygen-containing diluted gas mixture, the molecular oxygen can be that derived from purified oxygen, enriched oxygen or air; the gas for diluting can be one selected from the group consisting of $N_2$, CO, $CO_2$, and $H_2O$, or a mixture formed by several of them at any ratio. The oxidization reaction is conducted at a of from 220 to 450° C., preferably from 260 to 400° C., and a pressure of from 0.05 to 0.5 MPa, preferably at normal pressure; the overall space velocity of the gas mixture containing the raw material is in the range of from 500 to 5000 $h^{-1}$, preferably from 1000 to 3500$^{-1}$; the molar concentration of MAL is 1~20%, preferably 3~8%; the molar ratio between oxygen and MAL is 0.5~8:1, preferably 1~5:1; and the molar ratio between steam and MAL is 1~15:1, preferably 3~10:1. The conversion ratio and the selectivity of the MAA production via MAL oxidization are calculated according to the following equations:

Conversion of MAL=mole number of consumed MAL/mole number of fed MAL×100%;

Selectivity to MAA=mole number of produced MAA/mole number of consumed MAL×100%.

The present invention is described in more detail by the following detailed embodiments; however, the scope of this invention should not be limited to these examples.

Reference Example 1

Preparation of Fresh Catalyst 10,600 grams of ammonium paramolybdate, 290 grams of ammonium metavanadate, 420 grams of potassium hydroxide, and 200 grams of cesium nitrate were dissolved in 20 liters of distilled water to form solution A. 740 grams of phosphoric acid and 140 grams of arsenic acid were dissolved in 2 liters of water to form solution B. 570 grams of antimony trichloride were dissolved in 3,000 grams of 10 wt % diluted hydrochloric acid; then 360 grams of cupric nitrate was added to form solution C. Solution B was added into solution A with stirring, then solution C was added as well; pH of the resulting mixture was adjusted to 6 using aqua ammonia; then the mixture was heated to 70° C. and aged for 5 hours. The aged mixture was evaporated at 100° C. until dry and further dried at 110° C., and then fired at 250° C. for 3 hours in atmosphere to obtain a solid powder (a catalyst precursor). 8,500 grams of the resulting catalyst precursor powder were homogenously mixed with 1,500 grams of $ZrO_2$, and 1,500 grams of 1,4-t-butanediol were added thereto; the mixture obtained was molded into a cylindrical particle with a through hole in its longitudinal axis, which particle had an external diameter of 5 mm, an internal diameter of the through hole of 2 mm and a length of 5 mm, and said particle was calcined in atmosphere at 380° C. for 6 hours to obtain the finished catalyst.

1,300 grams of the catalyst particles were filled directly into a stationary bed tubular reactor having a diameter of 25 mm and a length of 3 m; a selective oxidation was conducted at 320° C. (hot spot) under normal pressure with molar ratio of MAL:$O_2$:$N_2$:$H_2O$ at 1:3:21:5 and overall space velocity at 1200 $h^{-1}$. Product was collected after 80 hours of reaction and analyzed by gas chromatography, as a result, the conversion of MAL was 80.4%, and the selectivity to MAA was 87.9%. The product obtained, from further reaction for 2,000 hours at aforementioned conditions, had the following analytic results: the conversion of MAL was 79.7%, and the selectivity to MAA was 88.1%, while no deterioration of the catalyst was observed.

Reference Example 2

Stability Test of the Catalyst

The fresh catalyst prepared in Reference Example 1 was used in gaseous selective oxidation of MAL to produce MAA, said oxidation occurred repeatedly for an extended period of time in order to obtain a deactivated catalyst. Reaction product was collected after 12,000 hours of gaseous selective oxidation of MAL to produce MAA, and analyzed by gas chromatography; as a result, the conversion of MAL was 32.1%, and the selectivity to MAA was 88.2%, while the catalyst was structurally deteriorated to become a deactivated catalyst and $MoO_3$ was formed.

Example 1

2,000 grams of the structural deteriorated catalyst (deactivated) from Reference Example 2 was ground to particles having a particle size of less than 40 mesh, loaded into a kneader, into which a mixture was gradually added, consisting of 100 grams of aqua ammonia, 130 grams of ammonium carbonate, 100 grams of distilled water and 80 grams of polyethylene glycol and kneaded for 30 minutes to form a catalyst paste; the paste was dried for 12 hours and then molded into a cylindrical particle with a through hole in its longitudinal axis; each of said particle had an external diameter of 5 mm, an internal diameter of 2 mm and a length of 5 mm, which particles were calcined at 380° C. in atmosphere for 6 hours to produce a regenerated catalyst whose keggin structure of heteropoly acid was fully recovered.

1300 grams of the catalyst particles were filled directly into a stationary bed tubular reactor having a diameter of 25 mm and a length of 3 m, a selective oxidation was conducted at 320° C. (hot spot) in atmosphere with a molar ratio of MAL:$O_2$:$N_2$:$H_2O$ being 1:3:21:5 and overall space velocity at 1200 $h^{-1}$. Product was collected after 80 hours of reaction and analyzed by gas chromatography; as a result, the conversion of MAL was 80.9%, and the selectivity to MAA was 87.8%. The product obtained, from further reaction for 2,000 hours at aforementioned conditions, had the following analytic results: the conversion of MAL was 80.7%, and the selectivity to MAA was 88.2%, while no deterioration of the catalyst was observed.

Example 2

The process and conditions for treating the deactivated catalyst in this example were the same as those of Example 1, except that the ammonium carbonate was replaced by 250 grams of ammonium acetate. The resulting regenerated catalyst from the treatment was used in oxidation of MAL to produce MAA at the same conditions as those in Example 1. Product was collected after 80 hours of reaction and analyzed by gas chromatography; as a result, the conversion of MAL was 76.9%, and the selectivity to MAA was 87.2%.

Example 3

The process and conditions for treating the deactivated catalyst in this example were the same as those in Example 1, except that the ammonium carbonate was replaced by 124 grams of ammonium chloride. The resulting regenerated catalyst from the treatment was used in oxidation of MAL to produce MAA at the same conditions as those in Example 1. Product was collected after 80 hours of reaction and analyzed by gas chromatography; as a result, the conversion of MAL was 74.6%, and the selectivity to MAA was 85.4%.

Example 4

The process and conditions for treating the deactivated catalyst in this example were the same as those in Example 1, except that the ammonium carbonate was replaced by 185 grams of ammonium nitrate. The resulting regenerated catalyst from the treatment was used in oxidation of MAL to produce MAA at the same conditions as those in Example 1. Product was collected after 80 hours of reaction and analyzed by gas chromatography; as a result, the conversion of MAL was 80.1%, and the selectivity to MAA was 87.7%.

Example 5

The process and conditions for treating the deactivated catalyst in this example were the same as those in Example 1 except that the amount of aqua ammonia was increased to 120 grams. The resulting regenerated catalyst from the treatment was used in oxidation of MAL to produce MAA at the same conditions as those in Example 1. Product was collected after 80 hours of reaction and analyzed by gas chromatography; as a result, the conversion of MAL was 78.8%, and the selectivity to MAA was 87.4%.

Example 6

The process and conditions for treating the deactivated catalyst in this example were the same as those in Example 1, except that the amount of ammonium carbonate was decreased to 100 grams. The resulting regenerated catalyst from the treatment was used in oxidation of MAL to produce MAA at the same conditions as those in Example 1. Product was collected after 80 hours of reaction and analyzed by gas chromatography; as a result, the conversion of MAL was 78.4%, and the selectivity to MAA was 87.9%.

Comparative Example 1

The process and conditions for treating the deactivated catalyst in this example were the same as those in Example 1, except that no ammonium carbonate was added. The resulting regenerated catalyst from the treatment was used in oxidation of MAL to produce MAA at the same conditions as those in Example 1. Product was collected after 80 hours of reaction and analyzed by gas chromatography; as a result, the conversion of MAL was 65.2%, and the selectivity to MAA was 89.1%.

Comparative Example 2

The process and conditions for treating the deactivated catalyst in this example were the same as those in Example 1, except that no aqua ammonia was added. The resulting regenerated catalyst from the treatment was used in oxidation of MAL to produce MAA at the same conditions as those in Example 1. Product was collected after 80 hours of reaction and analyzed by gas chromatography; as a result, the conversion of MAL was 54.6%, and the selectivity to MAA was 85.3%.

Example 7

The process and conditions for treating the deactivated catalyst in this example were the same as those in Example 1, except that the polyethylene glycol was replaced by t-butyl alcohol. The resulting regenerated catalyst from the treatment was used in oxidation of MAL to produce MAA at the same conditions as those in Example 1. Product was collected after 80 hours of reaction and analyzed by gas chromatography; as a result, the conversion of MAL was 77.1%, and the selectivity to MAA was 87.5%.

Example 8

The process and conditions for treating the deactivated catalyst in this example were the same as those in Example 1, except that the polyethylene glycol was replaced by pyridine. The resulting regenerated catalyst from the treatment was used in oxidation of MAL to produce MAA at the same conditions as those in Example 1. Product was collected after 80 hours of reaction and analyzed by gas chromatography, as a result; the conversion of MAL was 75.2%, and the selectivity to MAA was 88.1%.

Comparative Example 3

The process and conditions for treating the deactivated catalyst in this example were the same as those in Example 1, except that no polyethylene glycol was added. The resulting regenerated catalyst from the treatment was used in oxidation of MAL to produce MAA at the same conditions as those in Example 1. Product was collected after 80 hours of reaction and analyzed by gas chromatography; as a result, the conversion of MAL was 70.2%, and the selectivity to MAA was 88.4%.

What is claimed is:
1. A process for regenerating a deactivated heteropolymolybdophosphoric acid catalyst, the process comprising:
    grinding the deactivated catalyst into particles having a particle size of 40 mesh or less;
    mixing said particles with a mixture consisting of aqua ammonia, an aqueous solution containing ammonium ion, and an organic auxiliary, to obtain a particle-containing mixture;
        wherein the aqueous solution containing ammonium ion comprises a salt member selected from the group consisting of ammonium acetate, ammonium chloride, ammonium carbonate, and combinations thereof; and
        wherein the organic auxiliary is one or more selected from the group consisting of polyvinyl alcohol, t-butyl alcohol, and polyethylene glycol;
    kneading said particle-containing mixture in a kneader to obtain a paste;

drying the paste and molding the paste into a cylindrical particle with a through hole in its longitudinal axis; and heating the cylindrical particle in atmosphere at a temperature of from 350 to 450° C. for 1~10 hours to produce a regenerated catalyst.

2. The process for regenerating a deactivated catalyst according to claim 1, wherein the molar ratio between the ammonium ion in the mixture and the deactivated catalyst is 5:1~0.5:1; and the temperature of the mixture is controlled at 0~70° C.

3. The process for regenerating a deactivated catalyst according to claim 1, wherein the duration of the kneading is from 5 to 60 minutes.

4. The process for regenerating a deactivated catalyst according to claim 1, wherein the duration of the drying is from 1 to 24 hours.

5. The process for regenerating deactivated catalyst according to claim 1, wherein said particle-containing mixture contains said particles, aqua ammonia, water, the salt member, and one or more of the organic auxiliaries.

6. The process for regenerating a deactivated catalyst according to claim 1, wherein the cylindrical particle with a through hole in its longitudinal axis has an external diameter of from 4 to 8 mm, an internal diameter of from 0.5 to 3 mm and a length of from 3 to 8 mm.

7. The process for regenerating a deactivated catalyst according to claim 6, wherein the cylindrical particle with a through hole in its longitudinal axis has an external diameter of from 4 to 6 mm, an internal diameter of 1 to 2.5 mm and a length of from 4 to 6 mm.

8. The process for regenerating a deactivated catalyst according to claim 7, wherein the cylindrical particle with a through hole in its longitudinal axis has an external diameter of 5 mm, an internal diameter of 2 mm and a length of 5 mm.

9. The process for regenerating deactivated catalyst according to claim 1, wherein the aqueous solution containing ammonium ion contains water and the member selected from the group consisting of ammonium acetate, ammonium chloride, ammonium carbonate, and combinations thereof.

\* \* \* \* \*